(12) United States Patent
Lehe et al.

(10) Patent No.: US 6,605,097 B1
(45) Date of Patent: Aug. 12, 2003

(54) APPARATUS AND METHOD FOR TREATING FEMALE URINARY INCONTINENCE

(76) Inventors: Jorn Lehe, Willerstwiete 15, D22415 Hamburg (DE); Gene W. Kammerer, 14 Stephens Dr., East Brunswick, NJ (US) 08818

(*) Notice: Subject to any disclaimer, the term of this patent is extended or adjusted under 35 U.S.C. 154(b) by 0 days.

(21) Appl. No.: 09/691,359

(22) Filed: Oct. 18, 2000

(51) Int. Cl.[7] ............................................. A61B 17/04
(52) U.S. Cl. ........................ 606/148; 606/224; 606/227
(58) Field of Search .............................. 606/224, 225, 606/119, 148, 227, 185, 139, 144; 600/135–139; 128/898

(56) References Cited

U.S. PATENT DOCUMENTS

| | | | | |
|---|---|---|---|---|
| 3,892,240 A | * | 7/1975 | Park | 223/102 |
| 4,890,614 A | * | 1/1990 | Kawada et al. | 163/1 |
| 5,112,344 A | | 5/1992 | Petros | |
| 5,207,694 A | * | 5/1993 | Broome | 24/16 PB |
| 5,336,239 A | * | 8/1994 | Gimpelson | 606/223 |
| 5,342,374 A | * | 8/1994 | Wan et al. | 606/148 |
| 5,383,904 A | * | 1/1995 | Totakura et al. | 606/228 |
| 5,662,664 A | * | 9/1997 | Gordon et al. | 112/169 |
| 5,741,299 A | * | 4/1998 | Rudt | 606/224 |
| 5,899,909 A | | 5/1999 | Claren et al. | |
| 6,273,852 B1 | * | 8/2001 | Lehe et al. | 128/DIG. 25 |
| 2001/0053916 A1 | * | 12/2001 | Rioux | 606/139 |

FOREIGN PATENT DOCUMENTS

WO  WO 93/13714  *  7/1993  .......... A61G/17/04

* cited by examiner

Primary Examiner—David O. Reip
Assistant Examiner—Jake Davis

(57) ABSTRACT

A surgical instrument for introducing a support strand into the body to treat female urinary incontinence has an elongated, curved shaft with a distal end insertable into the body. The shaft has a lumen therein extending at least a portion of the length of the shaft through which the support strand may pass in an axial direction. The shaft has a slot on an exterior surface thereof communicating with the lumen allowing the support strand to be laterally passed between the lumen to a position outside the shaft. A pointed element, is removably positionable on the distal end of the shaft for facilitating the insertion of the shaft through the body and is connectable at one end to the support strand. The pointed element may either be swaged directly to the strand or be in the form of an elongated needle with an eye to which the strand is removably attached. In an associated method, the shaft sequentially delivers the pointed element through the body twice, forming a loop around the urethra to relieve incontinence. The slot in the shaft permits the instrument to be disassociated from the strand without disturbing the loop.

7 Claims, 4 Drawing Sheets

APPARATUS AND METHOD FOR TREATING FEMALE URINARY INCONTINENCE

FIELD OF THE INVENTION

The present invention relates to surgical methods and apparatus, and more particularly to a surgical apparatus and associated method for treating female urinary incontinence by implanting a support band.

BACKGROUND OF THE INVENTION

Surgical apparatus and methods are known for implanting a support band or filament extending between the abdominal wall and the tissue proximate to the urethra to reposition and support the urethra to compensate for over stressed ligaments causing incontinence. U.S. Pat. No. 5,112,344 to Petros and U.S. Pat. No. 5,899,909 to Claren et al., both of which are described further below, each disclose pointed, curved surgical instruments having a shape and dimensions permitting them to be introduced into the vagina, extended through the vaginal wall, around the pubic bone and through the abdominal wall for the purpose of placing the supportive surgical band or suture. The present invention provides an alternative apparatus and method to the foregoing.

SUMMARY OF THE INVENTION

The problems and disadvantages associated with the conventional techniques and devices utilized to place surgical supports to relieve female urinary incontinence are overcome by the present invention which includes a surgical instrument for introducing a support strand into the body to treat female urinary incontinence. The instrument has an elongated, curved shaft with a distal end insertable into the body. The shaft has a lumen therein extending at least a portion of the length of the shaft and terminating at the distal end and through which the support strand may pass in an axial direction. The shaft has a slot on an exterior surface thereof communicating with the lumen along at least a portion of the length thereof starting at the distal end with the slot allowing the support strand to be laterally passed between the lumen to a position outside the shaft. A pointed element, is removably positionable on the distal end of the shaft for facilitating the insertion of the shaft through the body and is connectable at one end to the support strand. The pointed element is dimensioned to prevent passage through the lumen when the shaft is inserted through the body. In accordance with an associated method, the instrument may be used to pass the strand through the vaginal wall and out the abdominal wall followed by a reinsertion of the instrument to carry the end of the strand terminating in the vagina through the vaginal wall and the abdominal wall to form a loop proximate the urethra. The slot in the shaft permits the instrument to be removed from the looped strand.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
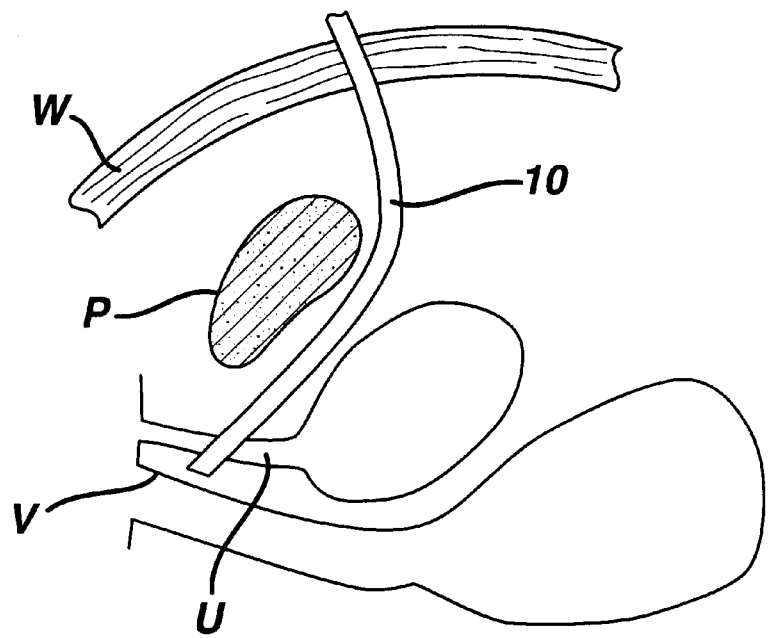
FIG. 1 is a diagrammatic sagittal cross-sectional view of the female genitourinary system with a urethral support tape in place.
Figure 2:
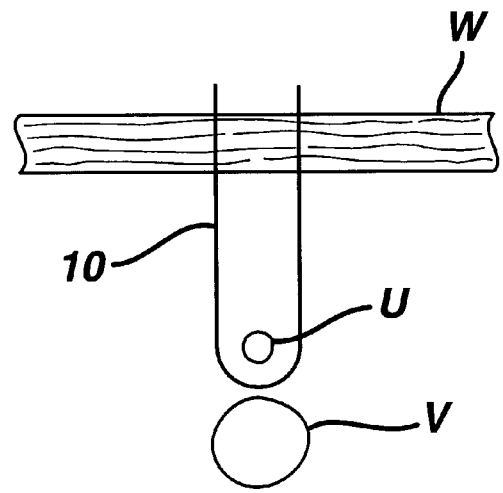
FIG. 2 is a diagrammatic front view of the genitourinary system with support tape of FIG. 1.

FIGS. 1 and 2 illustrate a support tape 10 looping around the urethra U, extending around the pubic bone P and through the abdominal wall W. The configuration shown in FIG. 1 may be achieved by known apparatus and methods but is also an objective of the present invention. For example, U.S. Pat. No. 5,899,909 discloses a surgical apparatus and method for introducing the tape 10 into the body in the position shown in FIG. 1, such patent being incorporated herein by reference for its teachings to that effect. More particularly, a length of the tape 10 is provided with a curved needle attached at each end with the points directed outwardly (see U.S. Pat. No. 5,899,909). A first needle is threadedly attached to an introducer handle and the needle is passed through an incision in the vaginal wall V, around the pubic bone P and through the anterior surface of the abdominal wall W. The introducer is detached from the first needle and attached to the second which is similarly guided through the body on the other side of the urethra U to create the supportive loop. To facilitate passage of the support tape 10 through the patient's tissues, the tape is covered by a smooth polymer sheath. After the tape 10 has been placed, the tape is cut to disconnect the needles and the smooth sheath withdrawn to allow the tape to grip the tissues through which it passes and allow tissue ingrowth. This apparatus is commercially available from Gynecare, a division of Ethicon, Inc. of Somerville, N.J.

Figure 3:
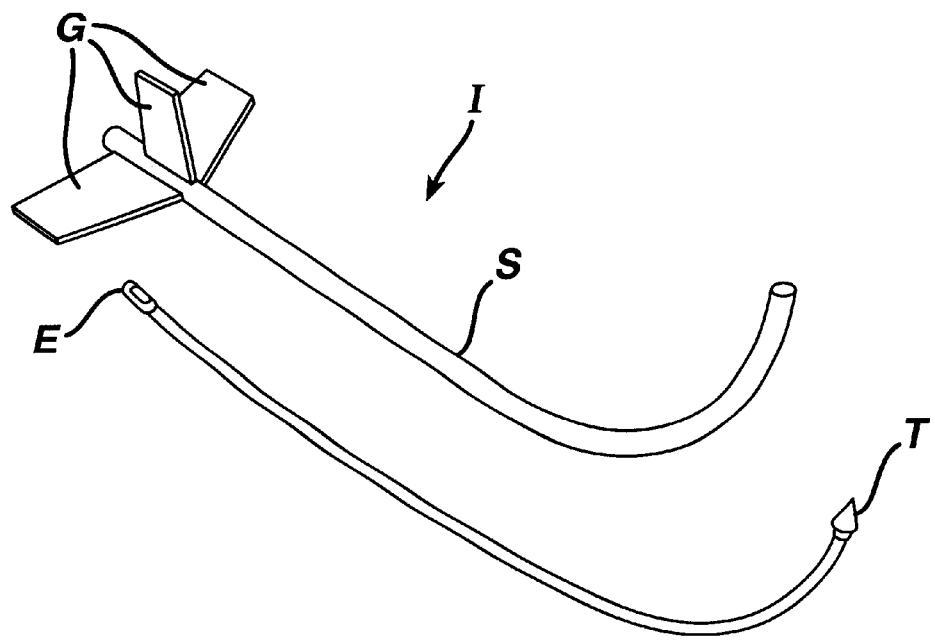
FIG. 3 is an exploded view of a surgical instrument as described in U.S. Pat. No. 5,112,344 to Petros.
Figure 4:
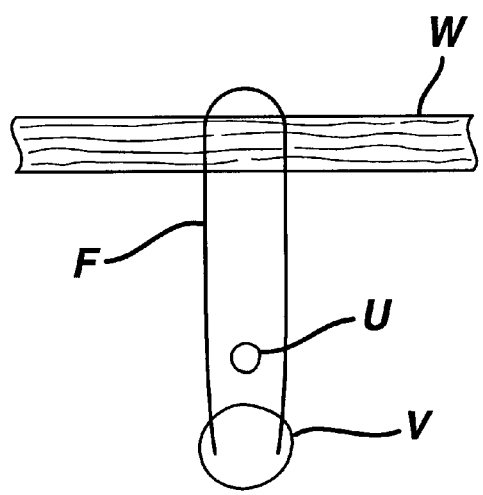
FIG. 4 is a diagrammatic view like FIG. 2, but showing an alternative tape position as known from the prior art.

An alternative surgical apparatus and method is described in U.S. Pat. No. 5,112,344 to Petros wherein a surgical instrument I like that shown in FIG. 3 is used to place a support filament F in the position shown in FIG. 4, such patent being incorporated herein by reference for its teaching to that effect. More specifically, the Petros instrument I has an elongated, curved shaft S slidably accommodating a flexible needle N having a pointed tip T and an eye E through which a filament F may be threaded. One or more gripping members G may be provided on the shaft S for leverage thereover. In accordance with the Petros '344 patent, the needle N may be placed within the shaft S and a filament F threaded through and tied through eye E. The needle N and shaft S combination is then guided into the vagina and the tip T penetrates the vaginal wall V. The shaft S and needle N are guided through the body in the generally arcuate path taken by the tape 10 of FIG. 1, such that the tip T protrudes through the abdominal wall, permitting the needle N to be withdrawn from the shaft S with the filament attached. The filament F is detached from the needle N allowing the shaft S to be withdrawn. Simultaneously, the filament F is held by the free end protruding from the abdominal wall, such that it remains in position. The needle N and shaft S are reassembled and reinserted into and through the vaginal wall V a second time, displaced to one side of the site of the first insertion. Upon protruding from the abdominal wall a second time, the needle N is withdrawn (no filament F is attached to it at this point) and the free end of the filament F extending from the abdominal wall as a consequence of the previous insertion of the instrument I is attached to the eye E of the needle N and the needle N is reinserted into the shaft S, thereby carrying the free end of the filament F into the vagina where it is detached, the needle N removed from the shaft S and the shaft S withdrawn from the body. As a result of the foregoing procedure, the filament forms a loop on the surface of the abdomen and the free ends of the filament extend into the vagina as shown in FIG. 4. The Petros '344 patent further teaches that the filament F may be withdrawn from the body after the development of scar tissue thereabout which functions as a ligament.

Figure 5A:
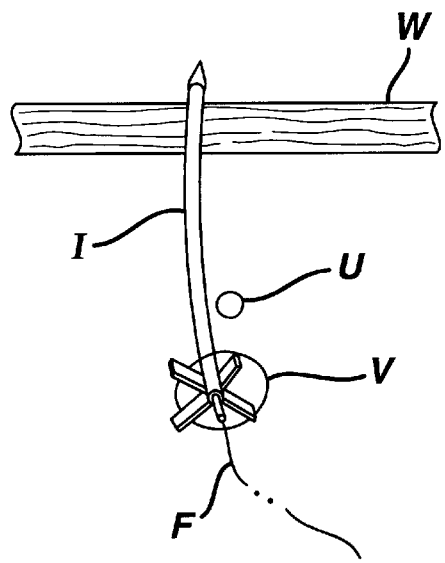
FIGS. 5a and 5b are sequential diagrams illustrating a limitation in the operation of the apparatus of Petros '344 in placing a support filament.
Figure 5B:
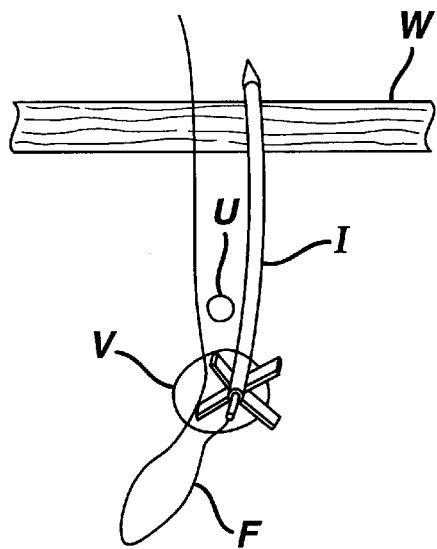

Referring to FIGS. 5a and 5b, it can be appreciated that an instrument I as shown in FIG. 3 can not be used to create a loop of filament F around urethra U when the instrument I is used to sequentially penetrate the body from the vagina V to the anterior surface of the abdominal wall W two times (A first penetration is shown in FIG. 5a and a second in FIG. 5b). More particularly, as shown in FIG. 5b, the instrument I itself becomes trapped in the loop of filament F preventing its removal without cutting the filament F.

Figure 6:
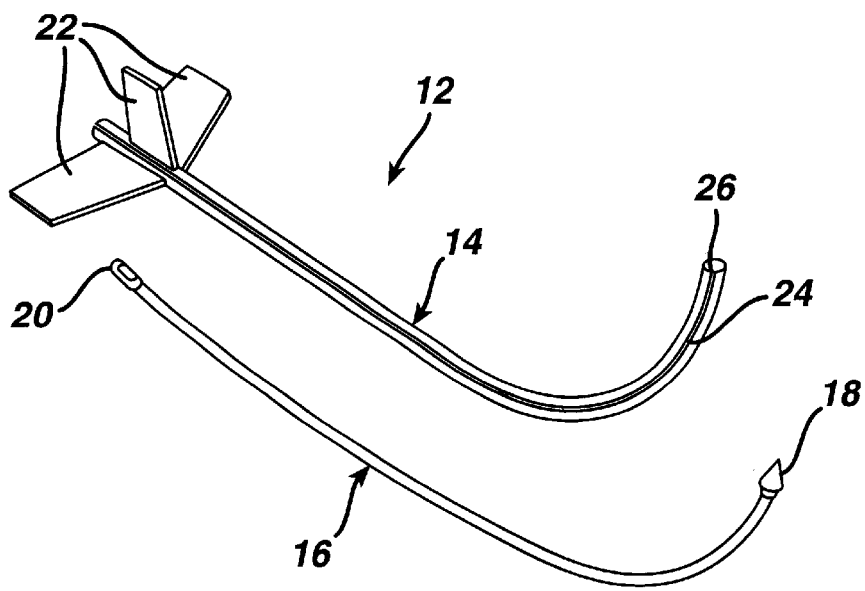
FIG. 6 is a perspective view of a surgical instrument in accordance with the present invention.

The apparatus 12 of the present invention is shown in FIG. 6 and is, in many respects, the same as the instrument I of FIG. 3, i.e., as taught by Petros '344. More specifically, the apparatus 12 has an elongated, curved shaft 14 accommodating a needle 16 having a pointed tip 18 at one end and an eye 20 at the other end. The shaft has a plurality of gripping members 22 extending from one end thereof. The apparatus 12 differs from that of Petros '344, however, in that the shaft 14 has a slot 24 extending along its length and communicating with the lumen 26 of the shaft 14. The slot 24 permits a filament F or support tape 10 as shown in FIG. 1 to be threaded laterally therethrough. The slot 24 can therefore remedy the situation depicted in FIG. 5b, viz., the slot 24 will permit the shaft 14 to be disassociated from the filament F by permitting the filament to pass through the slot 24 without disturbing the loop of filament F. Accordingly, the surgical procedure described in Petros '344 can be altered in the following manner. After the first insertion of the apparatus 12 which is used to carry a first portion of the filament F or support tape 10 from the vagina to the anterior surface of the abdominal wall W, the needle 16 can be inserted into the shaft 14 and the free end of the tape 10 extending from the vagina can be affixed to the eye 20 of the needle 16. The apparatus can then be reinserted into the vagina and through the vaginal wall at a position offset from the first position of insertion. When the tip 18 of the needle 16 penetrates the abdominal wall, the needle 16 can be withdrawn from the shaft 14 thereby pulling the free end of the tape 10 from the vagina through the body to an exterior position relative to the abdominal wall. The shaft 14 can then be withdrawn from the body and the suture or tape 10 can be threaded through the slot 24 to permit disassociation of the tape 10 from the shaft 14 and leaving the loop of tape 10 intact. The free ends of the tape 10 extending from the abdominal wall can then be pulled to exert the desired amount of tension on the tape 10 and the urethra. If the support tape 10 is going to be left in place permanently, the vaginal wall can be incised in a manner similar to that as disclosed in U.S. Pat. No. 5,899,909 to allow the tape to form a loop around the urethra beyond the vaginal wall.

Figure 7:
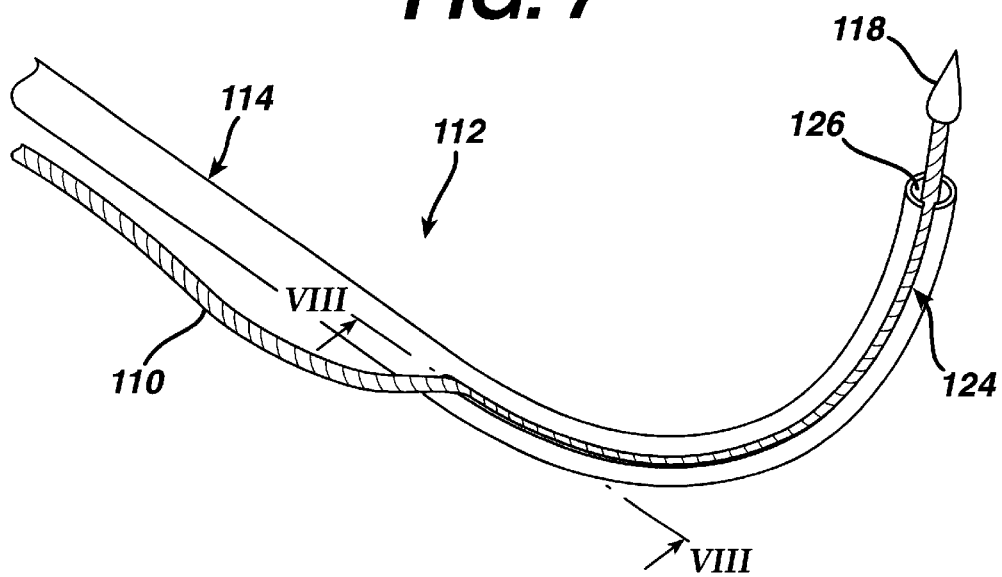
FIG. 7 is a perspective view of a surgical instrument in accordance with a second embodiment of the present invention.
Figure 8:
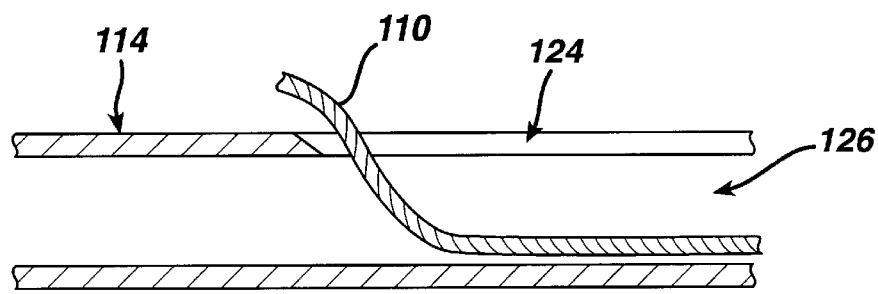
FIG. 8 is a cross-sectional view of the instrument of FIG. 7 taken along section line VIII—VIII and looking in the direction of the arrows.

FIGS. 7 and 8 show an alternative apparatus 112 having a similar shape and functionality as described above in reference to the apparatus 12 of FIG. 6. In the description to follow, a numbering convention will be used wherein elements having a similar function to a preceding embodiment shall have the same reference numerals increased by one hundred. In the apparatus 112 of FIG. 7, both ends of the support tape or filament 110 are swaged directly to a pointed tip 118 (only one end being shown in FIG.7). As before, the lumen 126 of the shaft 114 is smaller than the tip 118, such the tip 118 is supported on the end of the shaft 114 to pierce the tissue before it and admit the shaft 114 through the tissue. Unlike the previous embodiment, the slot 124 is truncated, extending only part of the way along the length of the shaft 114, starting near the end of the shaft 114 that supports the pointed tip 118. After the apparatus 112 is used to pass one side of the filament 110 through the body as above, the shaft 114 is withdrawn, disassociated from the filament 110, and the opposite side of the filament 110 loaded into the shaft 114 with the corresponding tip 118 held at the distal end. While FIG. 7 shows a filament 110 swaged directly to a pointed tip 118, a flexible needle 16 with an eye 20 and pointed tip 18 as shown in FIG. 6 could also be utilized as an element to which to attach the filament 110. In such case, the needle 16 need not be attached at both ends of the filament 110 and can be removably attached to the filament 110 for reuse as described in reference to FIG. 6.

Figure 9:
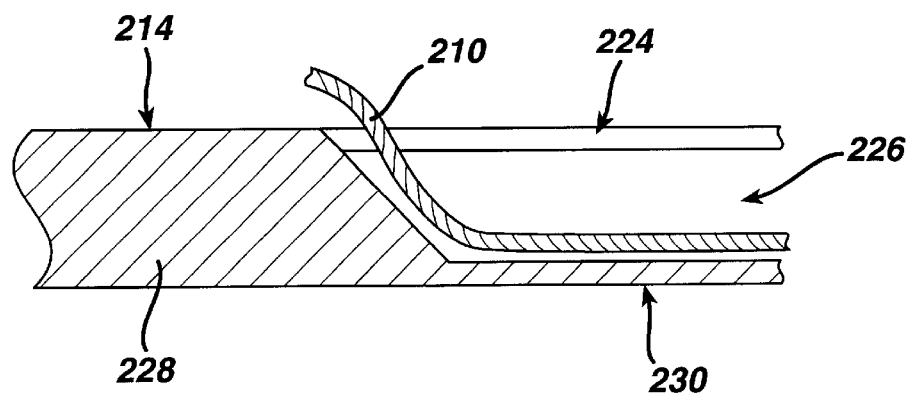
FIG. 9 is a cross-sectional view like FIG. 8, but showing a third embodiment of the present invention.

FIG. 9 illustrates that the shaft 214 need not be hollow along its entire length and has a solid portion 228, from which hollow portion 230 extends. The hollow portion 230 includes a lumen or slot extension 226 to accommodate the filament 210. The slot extension 226 can be milled into a solid shaft 214, formed by rolling a flattened section of the shaft 214 into a tubular shape, forged or cast.

It should be understood that the embodiments described herein are merely exemplary and that a person skilled in the art may make many variations and modifications without departing from the spirit and scope of the invention as defined in the appended claims.

We claim:

1. A surgical instrument for introducing a support strand into the body to treat female urinary incontinence, comprising:

an elongated, curved shaft having a distal end insertable into the body, said shaft having a lumen therein extending at least a portion of the length of said shaft and terminating at said distal end and through which the support strand may pass in an axial direction, said shaft having a slot on an exterior surface thereof communicating with said lumen along at least a portion of the length thereof starting at said distal end, said slot allowing the support strand to be laterally passed between said lumen to a position outside said shaft; and a pointed element, removably positionable on said distal end of said shaft, said pointed element facilitating the insertion of said shaft through the body and connectable at one end to the support strand, said pointed element being dimensioned to prevent passage through said lumen when said shaft is inserted through the body, wherein said pointed element is a flexible needle slidably receivable in said lumen and having a pointed tip at a first end and an eye at a second end, said eye removably receiving the strand therein.

2. The instrument of claim 1, wherein said slot is smaller than a diameter of said needle, preventing said needle from passing laterally through said slot and said needle has a length greater than said lumen such that said eye protrudes beyond said shaft when said needle is inserted within said lumen.

3. A surgical instrument for introducing a support strand into the body to treat female urinary incontinence, comprising:

an elongated, curved shaft having a distal end insertable into the body, said shaft having a lumen therein extending at least a portion of the length of said shaft and terminating at said distal end and through which the support strand may pass in an axial direction, said shaft having a slot on an exterior surface thereof communicating with said lumen along at least a portion of the length thereof starting at said distal end, said slot allowing the support strand to be laterally passed between said lumen to a position outside said shaft; and a pointed element, removably positionable on said distal end of said shaft, said pointed element facilitating the insertion of said shaft through the body and connectable at one end to the support strand, said pointed element being dimensioned to prevent passage through said lumen when said shaft is inserted through the body, wherein said shaft has a first portion with a solid cross-section and a second portion extending therefrom having said lumen therein.

4. A surgical instrument for introducing a support strand into a female patient's body to treat female urinary incontinence, comprising:

an elongated curved shaft having a distal end insertable into the body and a lumen therein extending at least a portion of the length of the shaft and terminating at the distal end and through which the support strand may pass in an axial direction, the shaft having a slot extending at least along a length of the lumen through which the strand may pass, the slot allowing the support strand to be passed between the lumen and a position outside the shaft thereby disassociating the support strand from the shaft; and a pointed element removably positioned on the distal end of the shaft and connectable at one end to the support strand, wherein when so positioned the pointed element facilitates insertion of the shaft through the body, the pointed element being dimensioned to prevent passage through the lumen when the shaft is inserted through the body;

wherein, when the pointed element is removably positioned on the distal end of the shaft and the shaft and pointed element are inserted into the body, the shaft and needle combination is dimensioned to extend from the patient's vaginal wall, around the patient's pubic bone and through the patient's abdominal wall, and wherein said pointed element is a flexible needle slidably receivable in the lumen of the shaft, and having a pointed tip at a first end.

5. The instrument of claim 4, in said flexible needle further comprises an eye at a second end, said eye removably receiving the strand therein.

6. The instrument of claim 5, wherein the slot is smaller than a diameter of the needle, preventing the needle from passing laterally through the slot and said needle has a length greater than the lumen such that the eye protrudes beyond the shaft when the needle is inserted within the lumen.

7. A surgical instrument for introducing a support strand into a female patient's body to treat female urinary incontinence, comprising:

an elongated curved shaft having a distal end insertable into the body and a lumen therein extending at least a portion of the length of the shaft and terminating at the distal end and through which the support strand may pass in an axial direction, the shaft having a slot extending at least along a length of the lumen through which the strand may pass, the slot allowing the support strand to be passed between the lumen and a position outside the shaft thereby disassociating the support strand from the shaft; and a pointed element removably positioned on the distal end of the shaft and connectable at one end to the support strand, wherein when so positioned the pointed element facilitates insertion of the shaft through the body, the pointed element being dimensioned to prevent passage through the lumen when the shaft is inserted through the body;

wherein, when the pointed element is removably positioned on the distal end of the shaft and the shaft and pointed element are inserted into the body, the shaft and needle combination is dimensioned to extend from the patient's vaginal wall, around the patient's pubic bone and through the patient's abdominal wall, and wherein the shaft has a first portion with a solid cross-section and a second portion extending therefrom having the lumen therein.

* * * * *

UNITED STATES PATENT AND TRADEMARK OFFICE
CERTIFICATE OF CORRECTION

PATENT NO.    : 6,605,097 B1
DATED         : August 12, 2003
INVENTOR(S)   : Jorn Lehe and Gene W. Kammerer It is certified that error appears in the above-identified patent and that said Letters Patent is hereby corrected as shown below:

<u>Column 6,</u>
Line 7, the word "in" should read -- wherein --.

Signed and Sealed this

Twenty-fifth Day of November, 2003

JAMES E. ROGAN
*Director of the United States Patent and Trademark Office*